United States Patent [19]
Simon

[11] Patent Number: 5,618,298
[45] Date of Patent: Apr. 8, 1997

[54] VASCULAR PROSTHESIS MADE OF RESORBABLE MATERIAL

[76] Inventor: Michael Simon, Am Hang 7A, 69226 Nussloch, Germany

[21] Appl. No.: 526,485

[22] Filed: Sep. 12, 1995

[51] Int. Cl.$^6$ .................................................. A61M 29/00
[52] U.S. Cl. ............................ 606/194; 606/195; 128/898
[58] Field of Search ........................... 128/898; 606/195, 606/194, 108, 198; 604/96, 97, 280; 623/1, 12

[56] References Cited

U.S. PATENT DOCUMENTS

| | | | |
|---|---|---|---|
| 5,061,275 | 10/1991 | Wallsten | 623/1 |
| 5,104,404 | 4/1992 | Wolff | 623/1 |
| 5,514,154 | 5/1996 | Lau et al. | 606/194 |

FOREIGN PATENT DOCUMENTS

| | | |
|---|---|---|
| 0428479 | 5/1991 | European Pat. Off. . |
| 0466105 | 1/1992 | European Pat. Off. . |
| 0528039 | 2/1993 | European Pat. Off. . |
| 2831360 | 2/1979 | Germany . |

OTHER PUBLICATIONS

Thrombogenicity of Heparin and Non–Heparin–Coated Catheters 1982 AJNR pp. 535–539, Sep. 1982.
Evaluation of Poly(L–Lactic Acid) As a Material for Intravascular Polymeric Stents, Biomaterials 1992, vol. 13, No. 3 pp. 176–182, Sep. 1990.

*Primary Examiner*—Michael Powell Buiz
*Assistant Examiner*—Kevin Truong
*Attorney, Agent, or Firm*—Baker & Daniels

[57] ABSTRACT

The invention relates to a method for the fabrication of a stent of a filiform material resorbable by the body, which stent is coated with heparin to avoid thromboses.

17 Claims, 1 Drawing Sheet

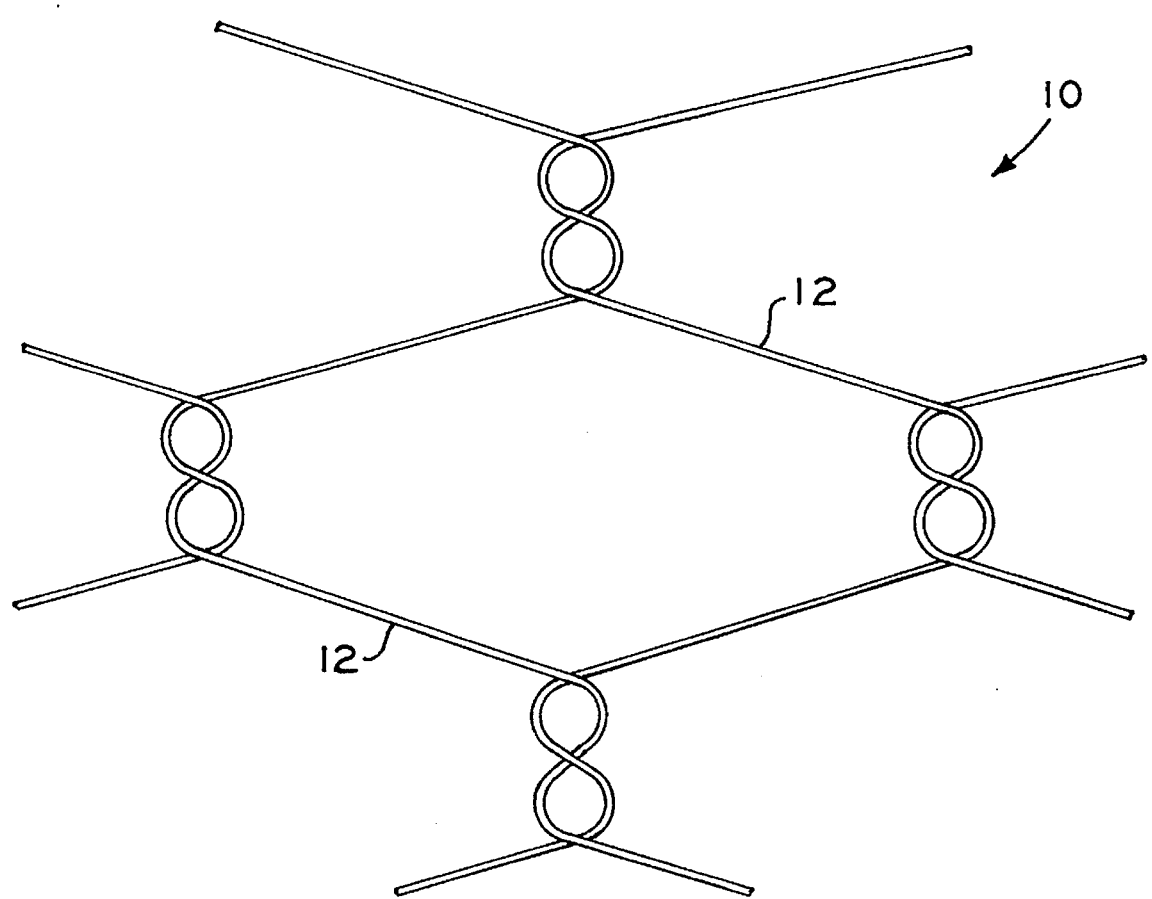
FIG_1
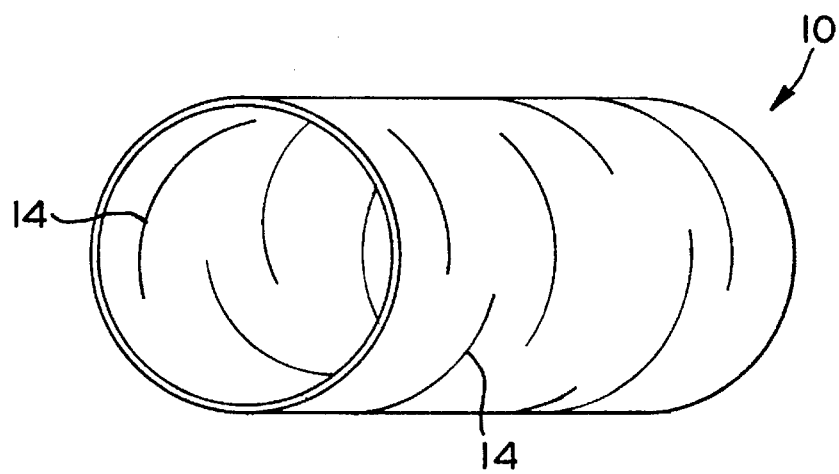
FIG_2

VASCULAR PROSTHESIS MADE OF RESORBABLE MATERIAL

BACKGROUND OF THE INVENTION

The invention relates to a method for making a stent coated with antithrombotic reagents, of filiform material resorbable by the body.

In balloon angioplasty of peripheral, renal and coronary arterial stenoses, a laceration of the vascular innermost skin, i.e., a dissection of the intima, may occur, which ultimately may lead to a vascular occlusion. Available as therapeutic measures are then an emergency bypass operation or the implantation of a vascular prothesis, or vascular support, of a so-called stent in the vessel. Such stents are tubular and reticulate implants inserted in the damaged vessel at reduced diameter and expanded to their final diameter only at the point in the vessel that is to be supported. The stent expands either due to its innate elasticity (so-called self-expanding stents) or expansion is brought about by a balloon which can be inflated inside the stent (so-called balloon-expandable stents). Prior stents consist normally of metal, for instance surgical refined steel, tantalum or nitinol; more recently, also stents of polymers have been proposed.

EP 0 466 105 A2 describes a vascular prosthesis which, however, from its structure, is not intended as a stent but more so as a vascular replacement. This vascular prothesis is not dilatable and, therefore, cannot be advanced such as a stent, by means of a catheter, through a blood vessel to a damaged site and positioned and dilated there. Furthermore, the core of this prior art document is constituted by providing a biocompatible interior surface of a vascular prothesis. Proposed for that purpose is the use of biological material, notably of collagen and elastin fibers, for making the inner coat. To stabilize this inner "biological" coat, a second, synthetic ply is externally applied on said coat.

U.S. Pat. No. 5,061,275 claims a stent fabricated of metal filaments. While plastic and biocompatible materials are mentioned also as stent material, only the fabrication of a stent of metal filaments of a specific alloy is described as the disclosed embodiment. This stent is subjected to a thermal treatment at 520° C., thereby fixing the metal filaments in their new form.

A considerable disadvantage of the prior stents, notably those of metal, is that they either remain as a permanent foreign body in the treated vessel or must be removed again in the course of a further operation.

To eliminate this problem, stents have been proposed which are made of material which the body can resorb. EP 0 428 479 A1 describes a stent of polycaprolactone, e.g.; also known are stents of poly-L-lactic acid, a material resorbable as well by the body (refer to Agrawal, C. M. et al. "Evaluation of Poly(L-lactic acid) as a material for intra-vascular stents"; Biomaterials, 13 (3), 176–182; 1992).

Common to all of the aforementioned stents is a pronounced thrombogeneity which, despite intensive medicamentous anticoagulation, may lead to a subacute stent thrombosis with formation of an infarct (with stents in coronary arteries). Meant by medicamentous anticoagulation is here the administration of anticoagulant substances which propagate throughout the entire system of blood vessels and, thus, result in anticoagulation in the entire system of blood vessels. A disadvantage of medicamentous anticoagulation is that wound healing problems occur also at the insertion site of the stent, mostly in the thigh or groin area, since blood coagulation is being suppressed also at this site.

EP 0 528 039 A1 describes a stent of filiform resorbable material, which stent is made by braiding and may be coated with antithrombotic reagents. Disadvantageous on the fabrication method of this stent is that the filiform braiding is prior to the thermal treatment removed from the forming cylinder, with the result that the stent shrinks during the subsequent thermal treatment.

DE-PS 28 31 360 describes the heparinization of a surface of a medical object wetted by the blood and which, however, does not consist of resorbable material. Arising from the resorbability of the material, though, are specific problems in conjunction with a heparin coating, and at that, notably a swift release of the heparin coating in the course of resorption. This is also why in using resorbable material it is mostly proposed to work the heparin into the resorbable material (refer to EP 0 528 039 A1), instead of applying it externally in one coat.

SUMMARY OF THE INVENTION

The objective underlying the present invention is to make a stent available which is made of resorbable material, avoids the cited disadvantages, is thus decomposed in the body and whose use diminishes the necessity of the heretofore customary medicamentous anticoagulation or makes it superfluous.

This objective is accomplished in that either the filiform material is wound around a forming cylinder of compressive and thermal stability and thereafter sintered at pressures between 100 and 2000 bars and elevated temperature, or that the filiform material is braided around a pressure and thermally stable form cylinder and then hardened at elevated temperature, with the stent removed then in both cases from the form cylinder being coated with heparin as an antithrombotic reagent.

The coating of surfaces with heparin is already known in principle. For example, Kido, D. K. et al. ("Thrombogeneity of Heparin- and Non-Heparin-Coated Catheters"; AJNR 3; 535–539; 1982) describes that heparin-coated cardiac catheters have a considerably lower thrombogeneity than catheters not coated with heparin. But these prior catheters were in use each for only one to two hours, and they did not consist of resorbable material.

Although the use of resorbable material, on the one hand, is known as such and, for another, also the basic option of the heparin coating of surfaces is previously known, no stent of heparin-coated resorbable material was heretofore proposed or known, despite grave disadvantages.

Coating the stent with heparin results in a local anticoagulation which is effective merely in the area of the stent and thus restricted to the area in which it is required. The other areas, in which at the same time a blood coagulation is desired, are thus not affected.

The fabrication of a stent according to the invention—described more generally—proceeds in a way such that the resorbable material is wound or knit (braided) in lattice or reticulate manner and given thereby a cylindrical shape. Next, this cylinder is treated thermally (hardened or sintered) and finally heparinized.

BRIEF DESCRIPTION OF THE DRAWINGS

FIG. 1 is an enlarged fragmentary drawing of the braided filaments; and

FIG. 2 is a perspective view of a braided stent according to the invention.

DETAILED DESCRIPTION

A stent fabricated, i.e., braided according to the second exemplary embodiment is harder than a stent made according to the first exemplary embodiment. As illustrated in FIG. 2, radial slots are provided in the stent after the sintering process; they facilitate expanding the stent longitudinally and thereby also reduce its diameter. Thereafter, the stent is removed from the cylinder serving as a form and is coated with heparin.

This heparin-coated stent of resorbable material can be realized with very small inside diameters, for example 2 mm, and is therefore very well suited especially for smaller vessels, notably coronary vessels. An effective local anticoagulation is especially important exactly with such small stents, since the risk of thrombus formation is disproportionately high.

The stent according to the invention is preferably fashioned balloon-expandable and can be introduced in the vessel to be supported in a known manner, the same as the other prior balloon-expandable stents. Stents made by sintering are stiffer than the hardened stents and can be made alternatively in a self-expanding form.

The following exemplary embodiments explain the fabrication of stents according to the present invention in more detail.

EXAMPLE 1

Used as starting material for the fabrication of an inventional stent 10 is synthetic, resorbable suture material of polyglycolic acid-trimethylene carbonate copolymerisate of filament size 6-0, corresponding to a filament diameter of 0.07 to 0.099 mm. Such material is known already as surgical suturing (refer to Katz, A. R. et al.: "A new synthetic monofilament absorbable suture made from polytrimethylene carbonate;" Surgery, Gynecology & Obstetrics 161, 213–222; 1985). Six, or also eight filaments—as illustrated in FIG. 1 for four filaments 12—were with double loopings wound on a thermally resistant metal cylinder with 4 mm outside diameter. The braiding was hardened with the metal cylinder for 30 minutes, in a nitrogen atmosphere at a temperature of 180° C. This was followed by a swift cooling in the flow of the inert gas. The hardened braiding was then removed from the metal cylinder and heparinized as follows, that is, coated with heparin:

In conjunction with the heparinization, the following solutions are needed:

Solution I

A: 9 mg of heparin, 22 ml of ultrapure water adjusted (at 60° C.) to pH 3.0 with HCl.
B: 24 mg of hexadecylamine hydrochloride/3 ml of ultrapure water adjusted (at 50° C.) to pH 3.0 with HCl.

The solution A is admixed to solution B at 60° C.; the resulting colloidal solution is diluted with ultrapure water to 125 ml.

Solution II 0.07 mg/ml heparin solution adjusted (at 50° C.) to pH 3.0 with HCl The treatment (exposure) of the braiding proceeded then as follows:

1 minute in solution I at 60° C., followed by
5× rinsing with distilled water, followed by
5 minutes in solution II at 60° C. followed by
5× rinsing with distilled water, followed by
repeating the entire process ten times.

In conclusion, the braiding was treated for 20 minutes at 60° C. with 0.25% glutaraldehyde solution and finally rinsed five times with distilled water.

Due to the amine surplus (hexadecylamine hydrochloride), the heparin molecules are enveloped by a double layer of this cationic surfactant, thus forming stable colloidal particles with a positive net charge. By adsorption of these positively charged particles to the stent braiding and reversal of the positively charged surface, by exposure in a heparin solution, heparin is thus bonded ionically to the braiding in several coats. The subsequent treatment with glutaraldehyde achieves a cross-linking of the heparin molecules.

EXAMPLE 2

Similar to Example 1, synthetic resorbable suture material of polyglycolic acid trimethylene carbonate copolymerisate of filament size 6-0 (filament diameter 0.07 to 0.099 mm) serves as starting material for the fabrication of a stent according to the invention.

The filaments were wound as closely as possible, in several (two to ten) layers, around a thermally and pressure-resistant metal cylinder with 4 mm outside diameter. Wound with suture material, this cylinder was introduced in a cylindrical bore of a thermally and pressure-resistant, notably two-part metal block. The cylindrical bore in the metal block has a diameter corresponding to the thickness of the wound filament layers, notably a slightly smaller diameter, and is realized, e.g., by appropriate butting of two metal blocks provided, each, on one end with groove-shaped recesses. The suture material was thermally treated for 10 minutes at a temperature of 180° C. and a pressure of 700 bars, that is, was sintered. To safeguard its deformability, the suture material sintered into a tube was provided with radial slots 14, each extending across about ¼ of the tube periphery (refer to FIG. 2). Next, the sintered sleeve was removed from the metal form cylinder and—the same as in Example 1—the coating with heparin carried out.

EXAMPLE 3

A synthetic resorbable suture material of polydioxanone with a filament diameter of 30 µm serves as starting material for the fabrication of an inventional stent. The filaments 12 were wound as closely as possible, in 25 layers, around a thermally and pressure-resistant metal cylinder with 4 mm outside diameter. Wound with suture material, this cylinder was introduced in a cylindrical bore in a thermally and pressure-resistant metal block such as described in Example 2. The suture material was treated thermally, that is, sintered, for 10 minutes at a temperature of 100° C. and a pressure of 700 bars. Cutting the radial slots 14 for assuring deformability as well as the following heparin coating were carried out as described in Example 2.

Stents of the type described above were tested in vitro. It was proved that the heparinized stents display actually a greatly reduced thrombogeneity as compared to stents not coated with heparin.

I claim:

1. Method for the fabrication of a stent coated with antithrombotic reagents, of filiform material resorbable by the body, comprising the steps of:

winding the filiform material on a form cylinder that is stable to pressure and stable thermally, subsequently sintering the wound filiform material at pressures between 100 to 2000 bars at elevated temperature to form a stent, removing the sintered stent from the form cylinder, and then coating the stent with heparin as an antithrombotic reagent.

2. Method for the fabrication of a stent according to claim 1 wherein a polyglycolic acid trimethylene carbonate copolymerisate and/or a polydioxanone is used as said filiform material resorbable by the body.

3. Method for the fabrication of a stent according to claim 1, wherein the stent is cylindrical and the cylindrical shape of the stent is formed by 2 to 50 tiered close windings of filiform material around a pressure and thermally stable form cylinder.

4. Method for the fabrication of a stent according to claim 3, where the filiform material consists of polyglycolic acid trimethylene carbonate copolymerisate, and wherein the step of sintering comprises giving the filiform material cylindrical shape at a pressure between 100 and 2000 bars subjected to a thermal treatment between 150° C. and 250° C.

5. Method for the fabrication of a stent according to claim 3, where the filiform material consists of polydioxanone, wherein the step of sintering comprises giving the filiform material cylindrical shape at a pressure between 100 and 2000 bars subjected to a thermal treatment between 50° C. and 150° C.

6. Method for the fabrication of a stent according to claim 3, where the filiform material consists of polyglycolic acid trimethylene carbonate copolymerisate, and wherein the step of sintering comprises giving the filiform material cylindrical shape at a pressure between 100 and 700 bars subjected to a thermal treatment between 170° C. and 190° C.

7. Method for the fabrication of a stent according to claim 3, where the filiform material consists of polydioxanone and wherein the step of sintering comprises giving the filiform material cylindrical shape at a pressure between 100 and 700 bars subjected to a thermal treatment between 80° C. and 120° C.

8. Method for the fabrication of a stent according to claim 1, wherein the stent is cylindrical and the cylindrical shape of the stent formed by 3 to 25 tiered close windings of filiform material around a pressure and thermally stable form cylinder.

9. Method for the fabrication of a stent coated with antithrombotic reagents, of filiform material resorbable by the body, comprising the steps of:

braiding the filiform material around a pressure and thermally stable form cylinder, thereafter hardening the braided filiform material at elevated temperature to form a stent, removing the hardened stent from the form cylinder, and then coating the stent with heparin as an antithrombotic reagent.

10. Method for the fabrication of a stent according to claim 9, wherein the step of braiding comprises braiding the filiform material on the form cylinder in double loopings.

11. Method for the fabrication of a stent according to claim 10, wherein a polyglycolic acid trimethylene carbonate copolymerisate and/or a polydioxanone is used as material resorbable by the body.

12. Method for the fabrication of a stent according to claim 10, wherein the step of braiding comprises braiding a plurality of filaments in double loopings on the pressure and thermally stable form cylinder so as to form a lattice type, or reticulate, cylinder.

13. Method for the fabrication of a stent according to claim 12 wherein said plurality of filaments consists essentially of 6 elements.

14. Method for the fabrication of a stent according to claim 12 wherein said plurality of filaments consists essentially of 8 elements.

15. Method for the fabrication of a stent according to claim 9, wherein the step of hardening comprises giving the filiform material a cylindrical shape at atmospheric pressure subjected to a thermal treatment between 150° C. and 250° C. in an inert atmosphere.

16. Method for the fabrication of a stent according to claim 9, wherein a polyglycolic acid trimethylene carbonate copolymerisate and/or a polydioxanone is used as material resorbable by the body.

17. Method for the fabrication of a stent according to claim 9, wherein the step of hardening comprises giving the filiform material a cylindrical shape at atmospheric pressure subjected to a thermal treatment between 170° C. and 190° C. in an inert atmosphere.

* * * * *